United States Patent
McCollough et al.

(10) Patent No.: US 9,386,936 B2
(45) Date of Patent: *Jul. 12, 2016

(54) DISTRIBUTED MICROWAVE IMAGE PROCESSING SYSTEM AND METHOD

(71) Applicant: ELLUMEN, INC., Arlington, VA (US)

(72) Inventors: William J. McCollough, Lorton, VA (US); Todd Robert McCollough, Barrington, IL (US)

(73) Assignee: ELLUMEN, INC., Arlington, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/798,428

(22) Filed: Mar. 13, 2013

(65) Prior Publication Data

US 2014/0276030 A1 Sep. 18, 2014

(51) Int. Cl.
*A61B 6/00* (2006.01)
*A61B 5/05* (2006.01)
(Continued)

(52) U.S. Cl.
CPC .............. *A61B 5/0507* (2013.01); *A61B 5/0013* (2013.01); *G06F 19/321* (2013.01); *G06F 19/328* (2013.01)

(58) Field of Classification Search
CPC .... A61B 5/0507; A61B 5/0013; G06F 19/32; G06F 19/321; G06F 19/324; G06F 19/328
USPC ......................................................... 600/430
See application file for complete search history.

(56) References Cited

U.S. PATENT DOCUMENTS

| | | |
|---|---|---|
| 5,103,181 A | 4/1992 | Gaisford et al. |
| 5,841,288 A | 11/1998 | Meaney et al. |
| 5,995,863 A | 11/1999 | Farace et al. |

(Continued)

FOREIGN PATENT DOCUMENTS

| | | |
|---|---|---|
| KR | 10-2011-0040520 A | 4/2011 |
| WO | WO 2011/163359 A2 | 12/2011 |

OTHER PUBLICATIONS

Gary A. Ybarra et al., Microwave Breast Imaging, Emerging Technology in Breast Imaging and Mammography, 2007, Chapter 16, pp. 1-12.

(Continued)

*Primary Examiner* — Ruth S Smith
(74) *Attorney, Agent, or Firm* — Foley & Lardner LLP

(57) ABSTRACT

A distributed imaging system uses non-ionizing radiation in the form of microwaves to image the body. This non-ionizing radiation is safer for a patient than traditional x-rays. The majority of image processing takes place in a centralized computing environment which receives microwave image data from many remote data acquisition sites (such as imaging centers, radiology groups, and/or doctor's offices). The centralized computing environment is specially configured to receive microwave image data from many sites and produce microwave images based on the received microwave image data. The microwave images may then be sent back to the acquisition site and/or to other sites for viewing and evaluation. This relieves the image data acquisition site of the burden and expense of having specialized high speed computer equipment that is necessary to produce microwave images. Because the computing environment collects and stores information (data and results) from many data acquisition sites in one central location, the prior results from all of the acquisition sites can be accessed and used to enhance processing and diagnosis.

17 Claims, 18 Drawing Sheets

(51) Int. Cl.
G06F 19/00 (2011.01)
A61B 5/00 (2006.01)

(56) References Cited

U.S. PATENT DOCUMENTS

| | | | |
|---|---|---|---|
| 6,433,720 B1 * | 8/2002 | Libove et al. | 341/144 |
| 6,448,788 B1 | 9/2002 | Meaney et al. | |
| 6,972,714 B1 | 12/2005 | Baharav et al. | |
| 7,040,168 B1 | 5/2006 | Merkel | |
| 7,132,836 B2 | 11/2006 | Peters et al. | |
| 7,280,227 B2 | 10/2007 | Merkel et al. | |
| 7,378,855 B2 | 5/2008 | Moshe | |
| 7,550,969 B2 | 6/2009 | Zhdanov | |
| 7,804,309 B2 | 9/2010 | Cummins | |
| 7,809,427 B2 | 10/2010 | Winters et al. | |
| 7,825,667 B2 | 11/2010 | Fang et al. | |
| 7,933,786 B2 * | 4/2011 | Wargin et al. | 705/4 |
| 8,095,204 B2 | 1/2012 | Smith et al. | |
| 8,400,168 B2 | 3/2013 | Troxler et al. | |
| 9,111,334 B2 * | 8/2015 | McCollough | G06T 11/005 |
| 2004/0077943 A1 | 4/2004 | Meaney et al. | |
| 2005/0203387 A1 * | 9/2005 | Godshalk et al. | 600/430 |
| 2008/0319285 A1 | 12/2008 | Hancock | |
| 2009/0273509 A1 | 11/2009 | Fullerton | |
| 2010/0113921 A1 | 5/2010 | Fear et al. | |
| 2011/0006785 A1 | 1/2011 | Gradinarsky | |
| 2011/0028825 A1 | 2/2011 | Douglas et al. | |
| 2011/0119212 A1 * | 5/2011 | De Bruin et al. | 706/12 |
| 2011/0130656 A1 | 6/2011 | Son et al. | |
| 2011/0169933 A1 | 7/2011 | Touboul | |
| 2012/0019406 A1 | 1/2012 | Sarkis | |
| 2012/0128265 A1 * | 5/2012 | Silver | G06T 11/006 382/275 |
| 2012/0158739 A1 * | 6/2012 | Ah-Pine et al. | 707/748 |
| 2012/0177267 A1 * | 7/2012 | Chen | A61B 6/5258 382/131 |
| 2012/0328076 A1 * | 12/2012 | Ikhlef | 378/62 |
| 2013/0018591 A1 | 1/2013 | Grzegorczyk | |
| 2014/0003699 A1 | 1/2014 | Moulik | |

OTHER PUBLICATIONS

Ann Franchois et al., Microwave Imaging-Complex Permittivity Reconstruction with a Levenberg-Marquardt Method, IEEE Transactions on Antennas and Propagation, Feb. 1997, pp. 203-215, vol. 45, No. 2.
Zhong Qing Zhang et al., Three Dimensional Nonlinear Image Reconstruction for Microwave Biomedical Imaging, IEEE Transactions on Biomedical Engineering, Mar. 2004, pp. 544-548, vol. 51, No. 3.
Elise C. Fear et al., Enhancing Breast Tumor Detection with Near-Field Imaging, IEEE Microwave Magazine, Mar. 2002, pp. 49-56.
Qing Huo Liu et al., Active Microwave Imaging I—2-D Forward and Inverse Scattering Methods, IEEE Transactions on Microwave Theory and Techniques, Jan. 2002, pp. 123-133, vol. 50, No. 1.
Xu Li et al., An Overview of Ultra-Wideband Microwave Imaging via Space-Time Beamforming for Early-Stage Breast-Cancer Detection, IEEE Antennas and Propagation Magazine, Feb. 2005, pp. 19-34, vol. 47, No. 1.
Elise C. Fear et al., Confocal Imaging for Breast Cancer Detection: Localization of Tumors in Three Dimensions, IEEE Transactions on Biomedical Engineering, Aug. 2002, pp. 812-822, vol. 49, No. 8.
Mariya Lazebnik et al., A Large-Scale Study of the Ultrawideband Microwave Dielectric Properties of Normal, Benign and Malignant Breast Tissues Obtained from Cancer Surgeries, 2007, Physics in Medicine and Biology, 52, pp. 6093-6115, IOP Publishing, UK.
Yao Xie et al., Multistatic Adaptive Microwave Imaging for Early Breast Cancer Detection, IEEE Transactions on Biomedical Engineering, Aug. 2006, pp. 1647-1657, vol. 53, No. 8.
Elise Fear et al., Microwaves for Breast Cancer Detection?, IEEE Potentials, 2003, pp. 12-18.
Natalia K. Nikolova, Microwave Imaging for Breast Cancer, IEEE Microwave Magazine, Dec. 2011, pp. 78-94.
Zastrow et al., Development of Anatomically Realistic Numerical Breast Phantoms With Accurate Dielectric Properties for Modeling Microwave Interactions With the Human Breast, IEEE Transactions on Biomedical Engineering, 2008, pp. 2792-2800, vol. 55, Issue 12.
James et al., Direct Use of CT Scans for Hyperthermia Treatment Planning, IEEE Transactions on Biomedical Engineering, 1992, pp. 845-851, vol. 39, Issue 8.
Chou et al., Development of a Rat Head Exposure System for Simulating Human Exposure to RF Fields from Handheld Wireless Telephones, Bioelectromagnetics, Suppl. Issue, n4, 1999, pp. 75-92.
Meaney et al., Clinical Microwave Tomographic Imaging of the Calcaneus: A First-in-Human Case Study of Two Subjects, IEEE Transaction on Biomedical Engineering, 2012, pp. 3304-3313.
U.S. Appl. No. 14/069,661, filed Nov. 1, 2013, McCollough et al.
C. Gabriel et al., The Dielectric Properties of Biological Tissues: I. Literature Survey, Phys. Med. Biol. 41, 1996, pp. 2231-2249.
J. Clegg et al., A Genetic Algorithm for Optimizing Multi-Pole Debye Models of Tissue Dielectric Properties, Phys. Med. Biol. 57, 2012, pp. 6227-6243.
Mariya Lazebnik et al., A Large-Scale Study of the Ultrawideband Microwave Dielectric Properties of Normal Breast Tissue Obtained From Reduction Surgeries, Phys. Med. Biol. 52, 2007, pp. 2637-2656.
S. Gabriel et al., The Dielectric Properties of Biological Tissues: II., Measurements in the Frequency Range 10 Hz to 20 Ghz, Phys. Med. Biol. 41, 1996, pp. 2251-2269.
S. Gabriel et al., The Dieletric Properties of Biological Tissues: III., Parametric Models for the Dielectric Spectrum of Tissues, Phys. Med. Biol. 41, 1996, pp. 2271-2293.
S. N. Hornsleth et al., A new CT Segmentation Algorithm for Finite Difference Based Treatment Planning Systems, Hyperthermic Oncology, 1996, vol. 2, pp. 521-523.
Uwe Schneider et al., The Calibration of CT Hounsfield Units for Radiotherapy Treatment Planning, Phys. Med. Biol., 41, 1996, pp. 111-124.
Wilfried Schneider et al., Correlation Between CT Numbers and Tissue Parameters Needed for Monte Carlo Simulations of Clinical Dose Distributions, Phys. Med. Biol. 45, 2000, pp. 459-478.
Andreas Christ et al., The Virtual Family—Development of Surface-Based Anatomical Models of Two Adults and Two Children for Dosimetric Simulations, Physics in Medicine and Biology 55, 2010, pp. N23-N38.
Christian Weber, Development of Patient-Specific Electromagnetic Model (PSEM) Based on MR Breast Images, Sep. 27, 2010, pp. 1-36.
D.C. Zhu et al., Brain Water Content Measurement and Visualization With Applications to Hydrocephalus, Proc. Intl. Soc. Mag. Reson. Med. 13, 2005, pp. 1099.
Daniel R. Messroghli et al., An Open-Source Software Tool for the Generation of Relazation Time Maps in Magnetic Resonance Imaging, BMC Medical IMaging, 2010, 10:16, pp. 1-8.
David C. Zhu et al., Full-Brain T1 Mapping Through Inversion Recovery Fast Spin Echo Imaging Wtih Time-Efficient Slice Ordering, Magnetic Resonance in Medicine, 54, 2005, pp. 725-731.
H. Neeb et al., A New Method for Fast Quantitative Mapping of Absolute Wate Content in Vivo,NeuroImage 31, 2006, pp. 1156-1168.
Hoi-Shun Lui et al., Development of Patient-Specific Breast Electromagnetic Model Based on Clinical Magnetic Resonance Images, IEEE, 2010, 4 pages.
J.M. Sill et al., Realistic Breast Models for Second Generation Tissue Sensing Adaptive Radar System, The Second European Conference on Antennas and Propagation, 2007, 4 pages.
M. Cavagnaro et al., Water Content Evaluation of a Human Tissue Using Magnetic Resonance Imaging: A Quantitative Benchmarking Approach, 2012 Internatinal Symposium on Electromagnetic Compatigility, IEEE, 2012, 6 pages.
M. Mazzurana et al., A Semi-Automatic Method for Developing an Anthropomorphic Numerical Model of Dielectric Anatomy by MRI, Physics in Meidcine and Biology 48, 2003, pp. 3157-3170.

(56) References Cited

OTHER PUBLICATIONS

M. R. Sentinella et al., Enhanced Continuous Tabu Search in a Hybrid Evolutionary Algorithm for the Optimization of Interplanetary Trajectories, 21st International Symposium on Space Flight Dynamics, 2009, Toulouse, France, 12 pages.

Mariya Lazebnik et al., Highly Accurate Debye Models for Normal and Malignant Breast Tissue Dielectric Properties at Microwave Frequencies, IEEE Microwave and Wireless Components Letters, vol. 17, No. 12, Dec. 2007, pp. 822-824.

Mark Converse et al., A Computational Study of Ultra-Wideband Versus Narrowband Microwave Hyperthermia for Breast Cancer Treatment, IEEE Transactions on Microwave Theory and Techniques, vol. 54, No. 5, May 2006, pp. 2169-2180.

Marta Cavagnaro et al., From Magnetic Resonance Imaging to Dielectric Properties of Tissues, Biophysics & Bioeng. Letters, 2011, vol. 4 (2), pp. 1-8.

P. Fatourous et al., Use of Magnetic Resonance Imaging for in Vivo Measurements of Water Content in Human Brain: Method and Normal Values, J. Neurosurg 90, Jan. 1999, pp. 109-115.

Paolo Farace et al., An Automated Method for Mapping Human Tissue Permittivities by MRI in Hyperthermia Treatemetn Planning, Phys. Med. Biol. 42, 1997, pp. 2159-2174.

Susan Rae Smith et al., Dielectric Properties of Low-Water-Content Tissues, Phys. Med. Biol, 1985, vol. 30, No. 9, pp. 965-973.

Thomas Meissner et al., The Complex Dielectric Constant of Pure and Sea Water From Microwae Satellite Observations, IEEE Transactions on Geoscience and Remote Sensing, vol. 42, No. 9, Sep. 2004, pp. 1836-1849.

USPTO Notice of Allowance, U.S. Appl. No. 14/069,661, Apr. 14, 2015, 10 pages.

USPTO Office Action, U.S. Appl. No. 14/069,661, Feb. 6, 2015, 19 pages.

\* cited by examiner

DISTRIBUTED MICROWAVE IMAGE PROCESSING SYSTEM AND METHOD

BACKGROUND OF THE INVENTION

The present invention relates generally to the field of image processing, and more specifically to a microwave image processing system.

Microwave imaging is a field of research that attempts to solve the inverse scattering problem. When radio frequency (RF) energy moves through air and impinges an object, scattering from the object occurs as the RF energy hits the surface and moves through the object. The idea of the inverse scattering problem is to measure this scattering field and, combined with other information about the object, determine an 'image' of the object that created the measured scattering field.

Microwaves are non-ionizing RF energy. Radiation that has enough energy to move atoms in a molecule around or cause them to vibrate, but not enough to remove electrons, is referred to as "non-ionizing radiation." Examples of this kind of radiation are sound waves, visible light, and microwaves. Ionizing radiation, on the other hand, is high-frequency radiation that has enough energy to remove an electron from (ionize) an atom or molecule. Ionizing frequencies have been shown to have cancer causing effects. Ionizing radiation has enough energy to damage the DNA in cells, which in turn may lead to cancer. Gamma rays, x-rays, some high-energy UV rays, and some sub-atomic particles such as alpha particles and protons are forms of ionizing radiation. The use of ionizing frequencies also has increased costs associated with their production and requires specialized environmental protections.

Efforts in microwave image processing involve researching and developing hardware and software solutions to the inverse scattering problem. The goal of this research is to develop methodologies, algorithms, hardware, systems, and techniques that allow users to completely image the human body in sufficient detail as to render a timely and accurate medical diagnosis by trained medical professionals.

SUMMARY OF THE INVENTION

Through the course of research it was discovered that the following problems must be solved:

Modeling of RF scattering problems on the scale of the human body is a very computationally intensive task. This modeling is called solving the forward scattering problem;

Solving the inverse scattering problem requires us to not only solve the forward scattering problem but then use additional computationally intensive algorithms to complete the solution for solving the inverse problem (i.e., create an image);

As a result, the overall solution to MWI (microwave imaging) is a computationally heavy and expensive endeavor that requires specialized computing techniques, hardware, and infrastructure that are not readily available.

What is needed in the field is a hardware and software platform designed specifically for processing microwave images. The ideal system would take advantage of parallel processing and optimized data storage and retrieval techniques in order to speed reconstruction of microwave images. The ideal system would also have a reconstruction algorithm specifically designed for reconstruction of microwave images. The ideal reconstruction software package would further include a learning algorithm that is able to learn from prior reconstructions and use the prior data to speed current reconstruction. The ideal system would further allow for viewing, diagnosis and reporting by medical professionals. Further, the ideal image processing system would provide for communications with research institutions and insurance companies.

A distributed imaging system is described below for imaging parts of a human body, or the entire human body, (or an animal body or part thereof) wherein non-ionizing radiation is used to image the body so that the imaging process is safer for patients than traditional x-rays. The majority of image processing takes place at a site specifically adapted for MWI, for example, a cloud based computing environment, thereby relieving the image data acquisition site and the image viewing location of the processing burden of image reconstruction. The distributed imaging system comprises an image data acquisition site, a computing environment, and a viewing location. The computing environment is remote from the acquisition site and viewing locations. The acquisition site has an image data capture device capable of capturing data for images of all or part of the human body. The capture device uses non-ionizing radiation, for example microwaves, to collect image data of the body thereby providing safer imaging for a patient requiring repeated imaging. The acquisition site also has a computing device with networking capabilities for transmitting the captured data as microwave image (MWI) data to the, for example, cloud based computing environment.

The computing environment receives the MWI data, processes the MWI data to reconstruct images, and makes the images available for viewing. The computing environment comprises at least two processors, at least two high-speed memory buses, and a plurality of memories that are connected to the processors by the high-speed memory buses. The computing environment includes: a raw image database that receives the MWI data from the acquisition site; an image reconstruction algorithm and MWI learning algorithm for processing the MWI data and reconstructing images; a reconstruction database for storing reconstructed images that are available for viewing; and, a MWI viewing application that allows for viewing of the reconstructed images.

The image viewing location includes a computing device that is able to access the computing environment over a network, and a display that allows a user to view selected images via a MWI viewing application. The image viewing location can be used by a doctor to view images, prepare a diagnosis, and submit a report on the patient. The viewing location can also be used by the patient to view images and reports. The viewing location can further be used by scientists doing research, and by insurance companies filing inquiries.

At the acquisition site, patient identification information is attached to the MWI data prior to transmission to the computing environment. At the computing environment, the MWI learning algorithm is able to provide the image reconstruction algorithm with prior data that is from prior reconstructions in order to speed reconstruction of the image. The computing environment further comprises at least one processing queue that receives data from the raw image database and provides the data to the processors. The at least two processors employ parallel computing techniques so that the processors operate in parallel on the MWI data. Further, the plurality of memories are specially configured for storage of MWI data so as to optimize the parallel operations of the processors.

The computing environment further comprises: a MWI patient reporting application that allows the user to prepare and submit reports on patients; a patient history database that stores and provides access to patient histories; and, a reporting database that stores and provides access to patient reports that have been submitted.

The computing environment further comprises: a patient diagnostic learning algorithm that provides the system with automated diagnostics of reconstructed images; a MWI data collaboration application that accepts and responds to insurance inquiries; and, a MWI DICOM (digital imaging and communications in medicine) communications application that allows researchers and scientists to access and communicate with the system.

In one preferred embodiment, the image data capture device is a full body scanner, and the non-ionizing radiation used by the image data capture device is in the range of 200-4000 MHz. Further, each of the at least two processors are preferably multi-core processors.

BRIEF DESCRIPTION OF THE DRAWINGS

Embodiments will now be described in more detail with reference to the accompanying drawings, given only by way of example, in which.

DETAILED DESCRIPTION OF EMBODIMENTS OF THE INVENTION

Figure 1:
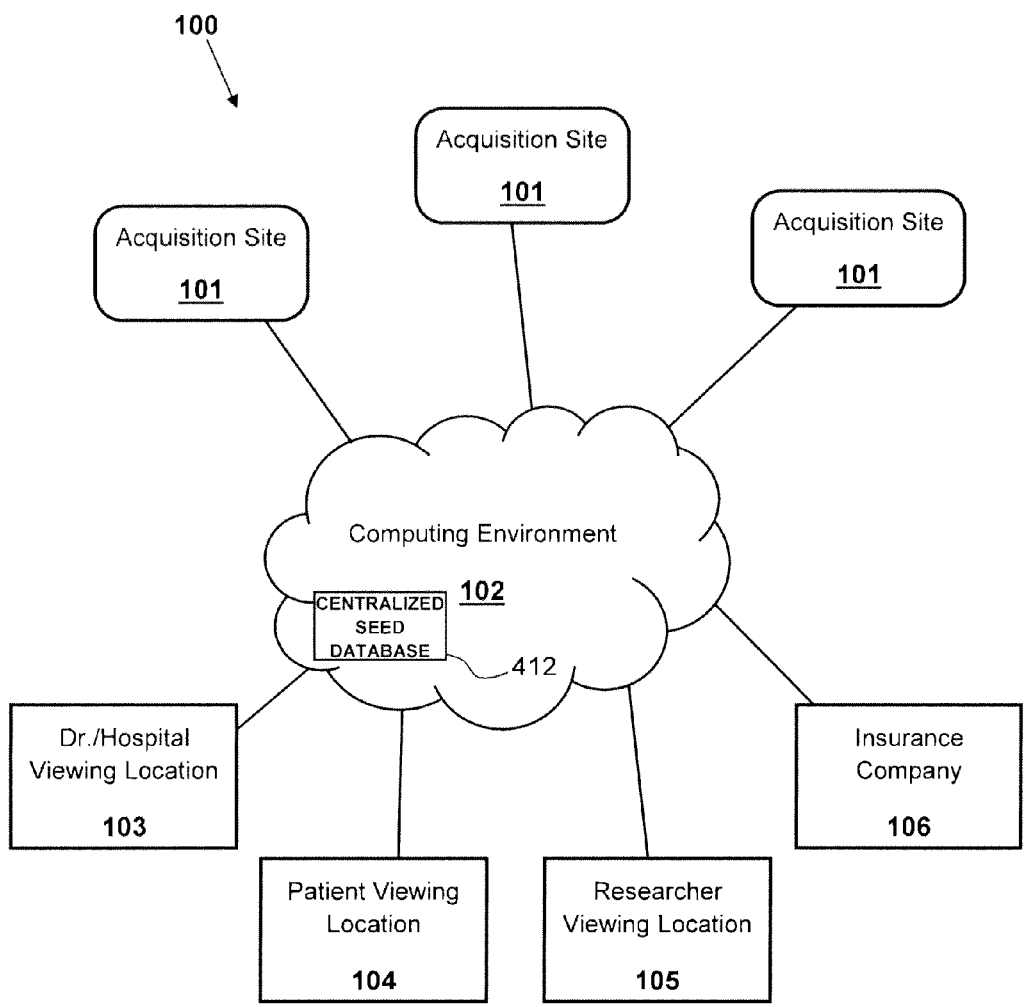
FIG. 1 is a simplified block diagram showing an overview of the present distributed microwave image processing system.

FIG. 1 shows an overview of the present distributed microwave image processing system 100. The present system 100 allows for removal of the computationally expensive task of image reconstruction from an image acquisition site 101, and from viewing locations (103-106). Image reconstruction is handled by a computing environment 102 that is specifically configured to quickly reconstruct microwave images. The present system 100 takes full advantage of the regular benefits of cloud computing, such as ease of access. However, there are also other advantages to cloud computing that are specific for microwave image (MWI) processing. These include:

Use of a centralized database of prior raw data from many acquisition sites and calculated images allows for the selection of a better "seed" (a better starting point for the iterative reconstruction calculation) which substantially reduces computation time.

MWI processing can be cost affordable because specialized and non-standard computing resources at scanner locations (acquisition sites) are not required;

Image viewing is more cost affordable because users do not have to implement software or specialized computers at their location;

Insurance reimbursements are cheaper and allows insurance companies to access data for medically reimbursed claims; and, Scientists and researchers have a central location to access all aspects of the MWI process for medical research purposes.

The acquisition site 101 can be in a hospital, a radiology group, a doctor's office, a medical imaging facility, or other site with a microwave image data capture device. A computer with network capabilities is also located at the acquisition site 101. After raw image data has been captured, the raw microwave image data is transmitted to the computing environment 102 for reconstruction of the image. Upon completion of reconstruction, the images are stored in a reconstruction database within the computing environment 102.

The microwave image processing for microwave imaging can make use of a conventional cloud environment augmented with components specific to MWI, including:

Platform Specific Parts:
RAW Scanner Database
RAW Scanner Processing Queue
Patient History Database
MWI Reconstruction Algorithms
MWI Learning Algorithms
Patient Diagnostic Learning Algorithms
Reporting Database
Application Specific Parts:
MWI Data Collaboration
MWI DICOM Communication
MWI Viewing Application
MWI Patient Reporting Application
Infrastructure Specific Parts:
MWI Computing Platforms for MWI reconstruction
Specialized Storage for MWI
Internal Specialized Networking for MWI A primary goal of the present system 100 is to allow users to completely image the human body in sufficient detail as to render a timely and accurate medical diagnosis by trained medical professionals. A doctor or other medical professional can access the computing environment 102 from viewing location 103, in order to view reconstructed images, diagnose the patient, and submit a report on the patient. The patient can access the computing environment 102 from viewing location 104, in order to view reconstructed images, review the patient's history, and provide updates to the patient's personal information. Scientists performing research can access the computing environment 102 from viewing location 105. The present system 100 preferably includes a Digital Imaging and Communications in Medicine (DICOM) communications application to communicate with researchers in an industry standard format. Insurance companies can access and communicate with the system via viewing location 106 that includes a Data Collaboration application that provides for communications in insurance industry standards.

In most embodiments, the computing environment 102 is located remote from acquisition sites 101, viewing locations 103-105, and insurance company 106. In many embodiments, the environment 102 is located many miles away (for example more than 10 or more than 100 miles away) from sites 101, locations 103-105 and/or company 106. However, in certain applications of the invention, "remote" as used herein can mean in a different room or in a different building.

The environment 102 contains a centralized database 412 of prior raw microwave data along with the resulting calculated images and other information previously calculated for the acquisition sites 101. This centralized database is a significant feature because it includes raw data (and calculated images and other information) from a plurality of acquisition sites 101 (for example, 10 or more sites or 100 or more sites) and thus the processing for an individual site 101 is able to take advantage of prior calculations done for all of the sites in the distributed system 100. Since calculation of a microwave image is an iterative process which requires a seed (an educated guess as to the electrical properties of the subject patient) as a starting point, the use of prior results from calculations done for all of sites 101 results in a better seed, and thus a substantial reduction in computing.

The centralized database may also collect the images and resulting diagnosis from all of the sites in the distributed system, which results in a more informed automated diagnostic algorithm.

Background on microwave imaging is set forth in the following texts: Matteo Pastorino, "Microwave Imaging," WILEY, 2010; Jaleel Akhtar, "Microwave Imaging: Reconstruction of One Dimensional Permittivity Profiles," VDM Verlag, 2008; and Bindu Gopinathan Nair, "Active Microwave Imaging for Mammography: Microwave Medical Imaging," Lap Lambert Academic Publishing, 2012. The entire contents of all three of these texts is incorporated herein by reference for the hardware, software, components, techniques, algorithms, data, and mathematical techniques described therein related to microwave and other types of non-ionizing radiation imaging.

Figure 2:
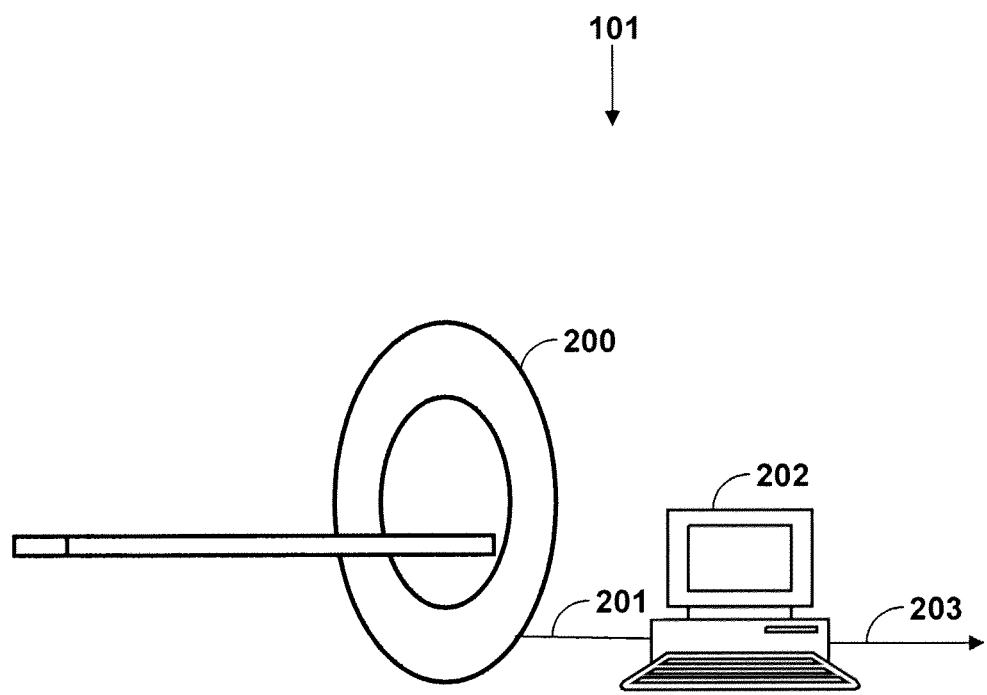
FIG. 2 shows an exemplary image acquisition site.

FIG. 2 shows an exemplary image data acquisition site 101. The exemplary image acquisition site 101 includes an image capture device 200 connected via link 201 to a computer 202, wherein the computer is connected to a network via link 203. Links 201 & 203 can be wired or wireless links. The image capture device 200 is preferably a full body scanner that uses non-ionizing frequencies, such as microwaves, to image the body. Ionizing frequencies have been shown to have cancer causing effects, increased costs associated with their use, and require specialized environmental protections. The non-ionizing microwaves used by the image capture device 200 are preferably in the range of 200-4000 Megahertz (MHz). The present system 100 moves the computationally expensive tasks into the cloud and away from the image data acquisition site 101. Thus, allowing simpler and less expensive equipment to be used at the acquisition site 101.

Figure 3:
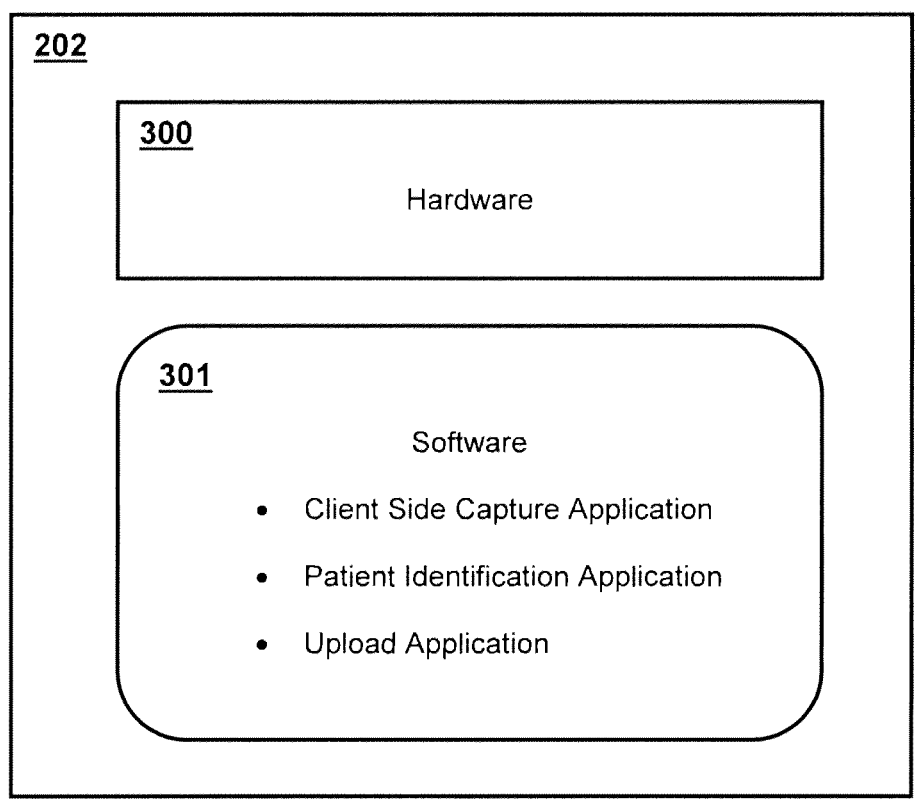
FIG. 3 is a block diagram of an exemplary computing device at the acquisition site.

FIG. 3 is a block diagram of an exemplary computing device 202 at the image acquisition site 101. Computer 202 includes appropriate hardware 300 and software 301. The software 301 includes: a Client Side Capture Application; a Patient Identification Application; and, an Upload Application. The Client Side Capture Application is used to consolidate image data from the capture device 200, attach patient information from the Patient Identification Application to the image data to create MWI Data, and forward the MWI Data to the Upload Application. The Upload Application is responsible for transmitting the MWI Data with attached patient information to the Computing Environment 102.

Figure 4:
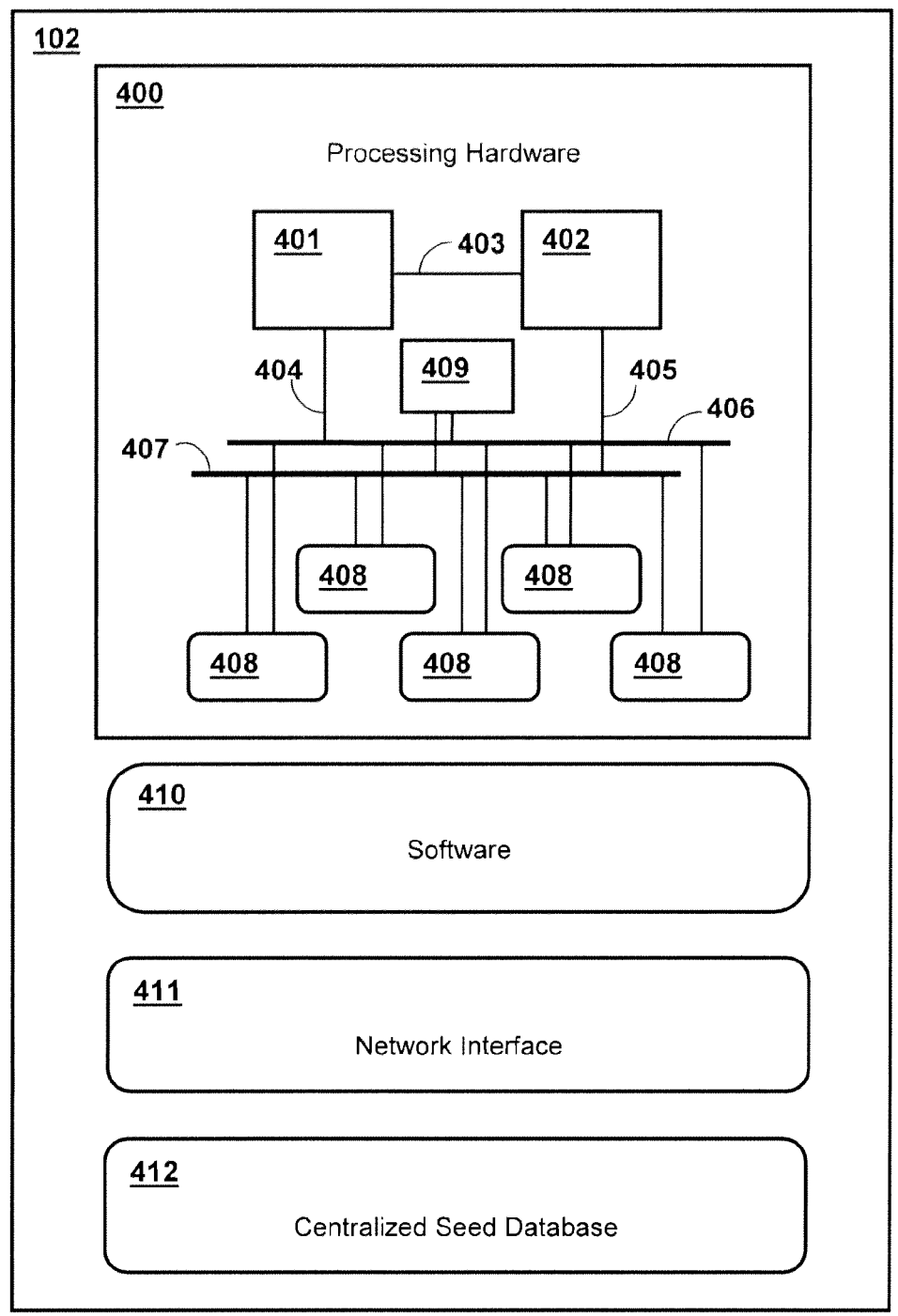
FIG. 4 is a block diagram of an exemplary computing environment showing exemplary hardware modules.

FIG. 4 is a block diagram of an exemplary computing environment 102 that provides a specialized MWI computing platform specifically configured to meet the requirements of MWI processing. Preferably, both processors 401 & 402 are multicore processors, and the two processors 401 & 402 employ parallel computing techniques. High-speed link 403 is used to connect the processors 401 & 402 in order to provide processor to processor communications. Internal high-speed memory buses 406 & 407 provide optimized access to memory modules 408. Processor 401 is connected to high-speed memory bus 406 via connection link 404, and processor 402 is connected to high-speed memory bus 407 via connection link 405. Processing queue 409 is connected to both high-speed memory buses 406 & 407. Processing queue 409 provides MWI data from the memory modules to both processors 401 & 402 in order to support parallel operations by the processors during reconstruction of images. In one preferred embodiment, the two processors are employed in two high performance computers (HPC's) networked together using Infiniband® network cards. Optical cables and specialized network switches are also employed to speed communications in the computing environment. The HPC's are assisted by GPU (graphics processing unit) processing cards that offer processing help in a specific subset of calculations.

Software module 410 provides the programs, algorithms, applications and other software required by the computing environment 102. Further details of the software module 410 are provided in conjunction with FIG. 5.

Network Interface module 411 provides the necessary components and software modules for interfacing with the Internet, other networks, the acquisition sites 101, the multiple viewing locations 103-105, and with the insurance company 106.

Other configurations of the computing environment are possible. A main feature is that the environment be built for computational speed, preferably using parallel computing components including high speed RAM and disk drives. The aggregate computation performance of the computational environment is preferably greater than 10 Teraflops for example, 15 Teraflops, 25 Teraflops or more. In an alternate embodiment, a head node acts as a controller for compute jobs in the high-speed computational environment. The job of the head node also includes task scheduling, resource allocation, and other relevant tasks to support computing in a parallel environment. A typical CPU will have multiple processors having at least 40 total cores, 256 GB RAM, and 2 Terabytes of Data Storage. The computing environment has multiple CPUs of this capability. Data Communication between the major systems utilizes high-speed fiber optic communications running typically greater than 40 GB/s. Data Communications within a major system parallel data path run typically greater than 4.80 GT/s (Giga-transfers per second). Further, a powerful supplemental computational platform is constructed from external graphical processing units (GPU). The computing environment includes 4 to 16 or more GPUs that are merged into the overall computing environment, and are accessible as a general processing node. Finally, a high-speed data bus interconnecting GPUs is provided for shared memory/processor access, and a high-speed data port for communicating results to the outside world is provided.

Figure 5:
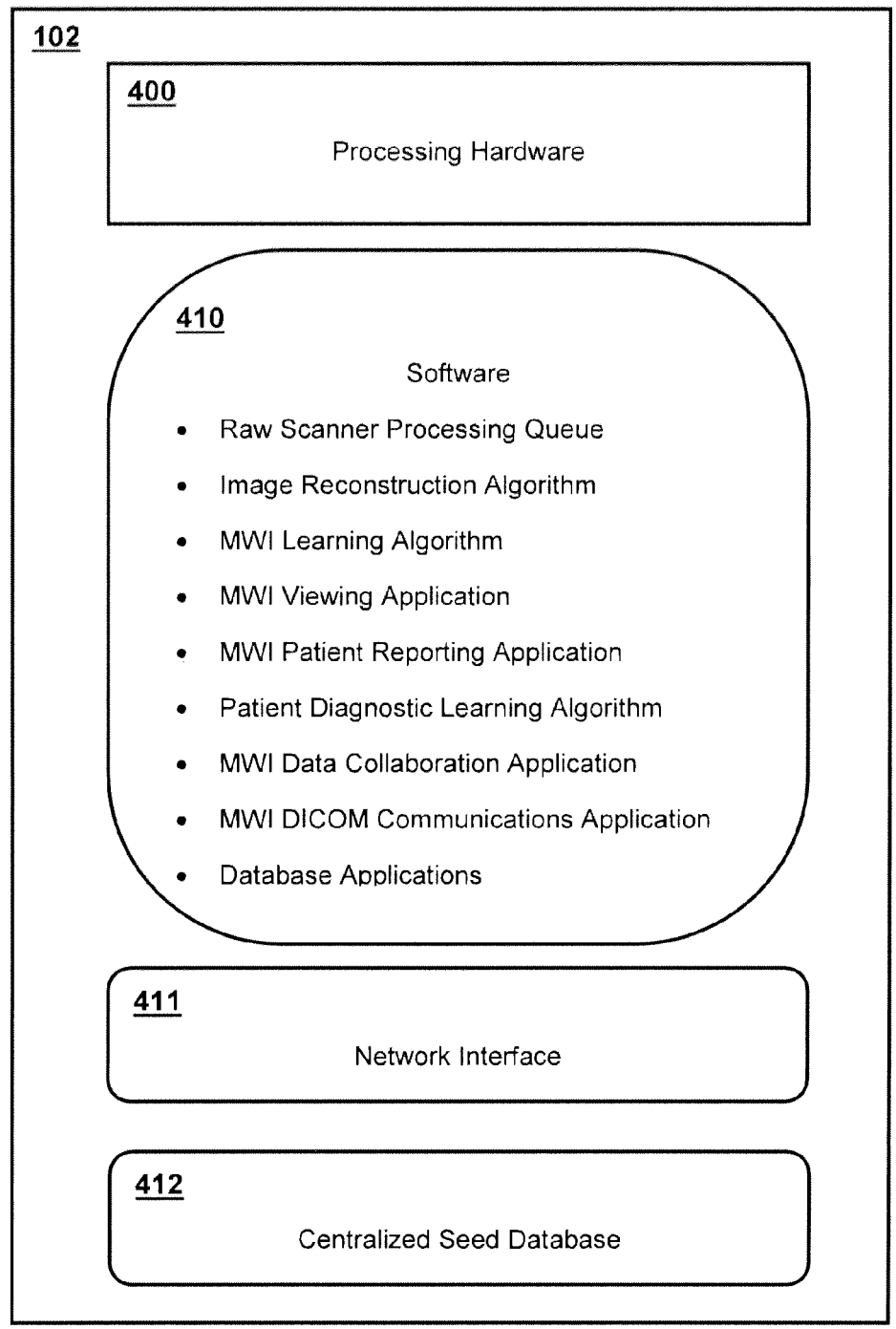
FIG. 5 is a block diagram of the exemplary computing environment showing exemplary software modules.

FIG. 5 illustrates exemplary software 410 in the computing environment 102. A Raw Scanner Processing Queue application provides for receiving raw scanner data from the acquisition site, storing the data in a manner consistent with parallel processing, and providing the data to the processing hardware 400 during reconstruction. The Image Reconstruction Algorithm was developed to process the raw MWI data, and take advantage of the specialized platform provided in the processing hardware 400. The MWI Learning Algorithm accelerates reconstruction by providing data from prior reconstructions to the reconstruction algorithm. The Learning Algorithm is updated upon completion of each reconstruction. The MWI Viewing Application allows for selected viewing of reconstructed images by doctors, medical professionals, research scientists and patients. A client-side MWI viewing application is also provided at the different viewing locations of the system. The Patient Reporting Application allows doctors and clinicians to prepare and submit reports on patients. The Patient Diagnostic Learning Algorithm assists the doctors and clinicians in diagnosing patients. The Diagnostic Learning Algorithm can track changes in a patient's images, and also identify suspect anomalies in images. The MWI Data Collaboration Application allows for communications with insurance companies. Direct communications with insurance companies allows for a smooth flow of operations between the patient and the healthcare facility. The MWI DICOM Communications Application allows scientists and other researchers to access and communicate with the present system. The Database Applications module provides for the creation and maintenance of multiple databases used by the system. The primary databases used by the system include the Raw Scanner DB, the Reconstruction DB, the Reporting DB, and the Patient History DB.

Figure 6:
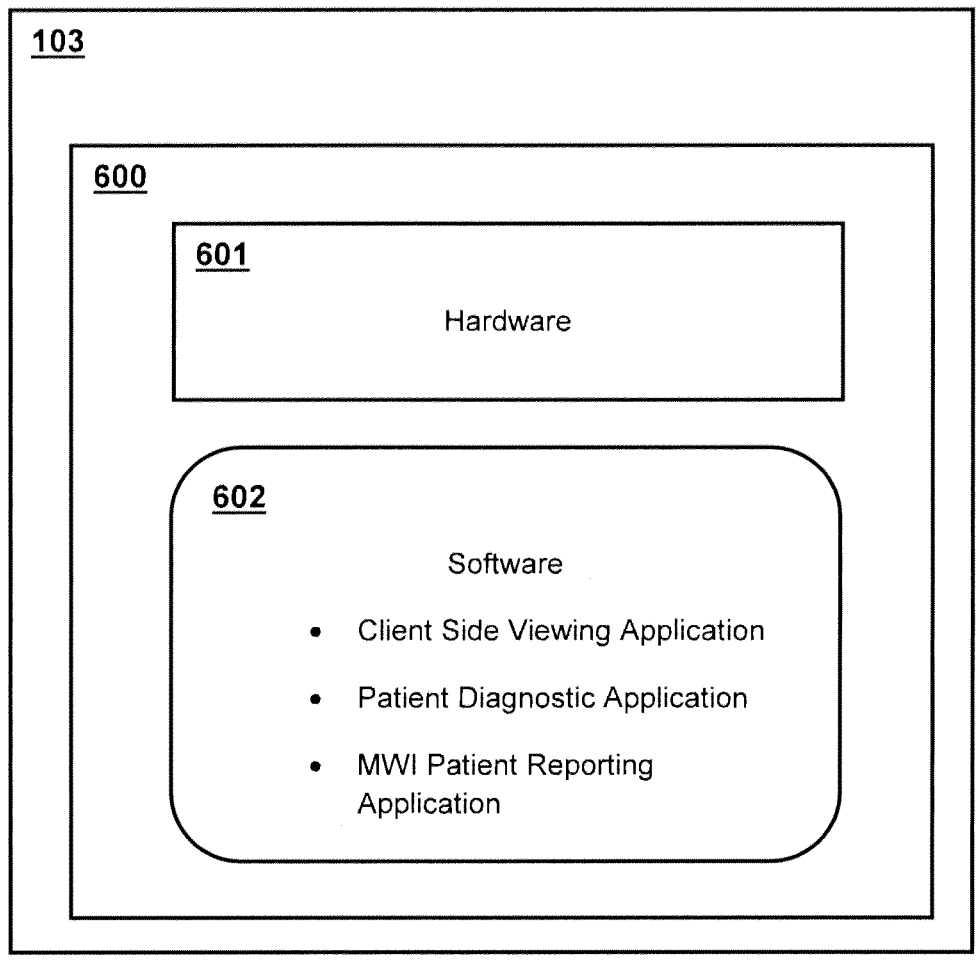
FIG. 6 is a block diagram of an exemplary computing device at the viewing location of a medical professional.

FIG. 6 is a block diagram of an exemplary computing device 600 at the viewing location 103 of a medical professional. The computing device 600 is preferably a networked computer with hardware 601 for connecting to a network, accepting input from a user, and displaying reconstructed images and other data to the medical professional. The computing device 600 preferably includes software 602 that aids the medical professional in viewing reconstructed images, diagnosing patients, and preparing reports on patients. The Client Side Viewing Application is tailored toward the medical professional and allows them to sign-in to the system and be presented with a menu of personalized options, including a list of patients associated with the medical professional.

Figure 7:
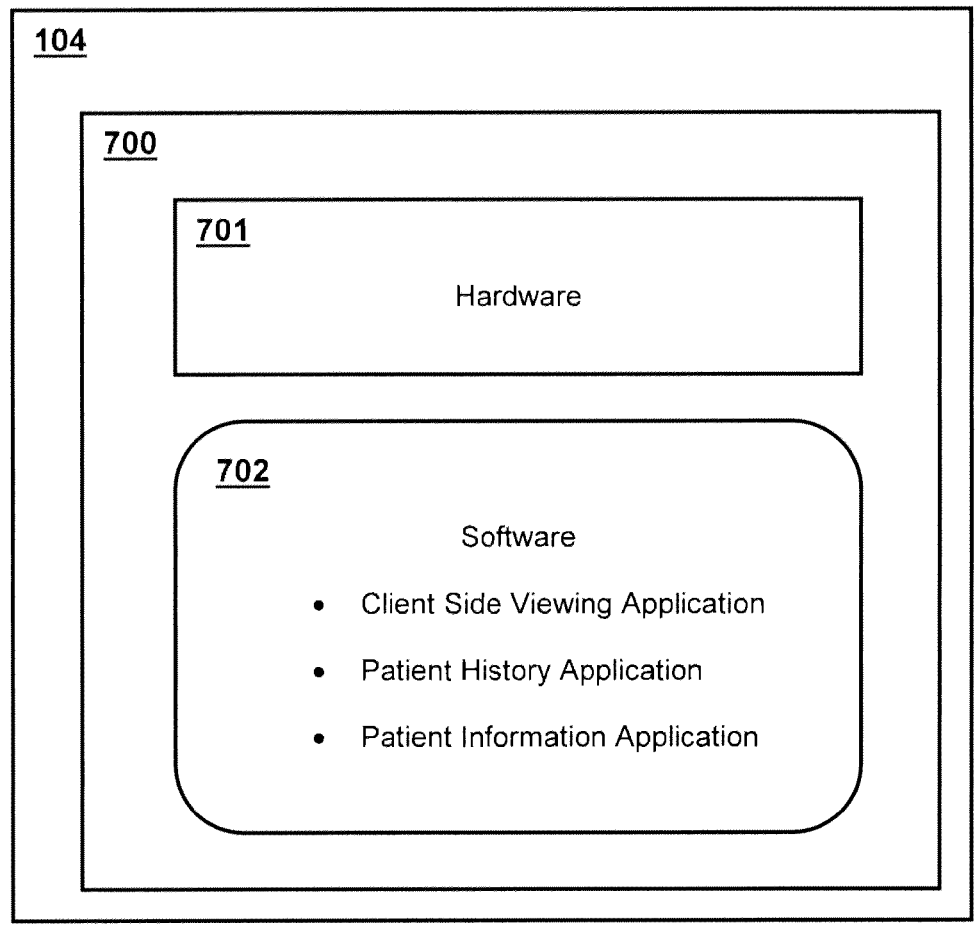
FIG. 7 is a block diagram of an exemplary computing device at the viewing location of a patient.

FIG. 7 is a block diagram of an exemplary computing device 700 at the viewing location 104 of a patient. The computing device 700 is preferably a networked computer with hardware 701 for connecting to a network, accepting input from a user, and displaying reconstructed images and other data to the patient. The computing device 700 preferably includes software 702 that aids the patient in viewing reconstructed images, the patient's history, and providing updated personal information regarding the patient. The Client Side Viewing Application is tailored for the patient and allows them to sign-in to the system and be presented with a menu of personalized options relating to the patient.

Figure 8:
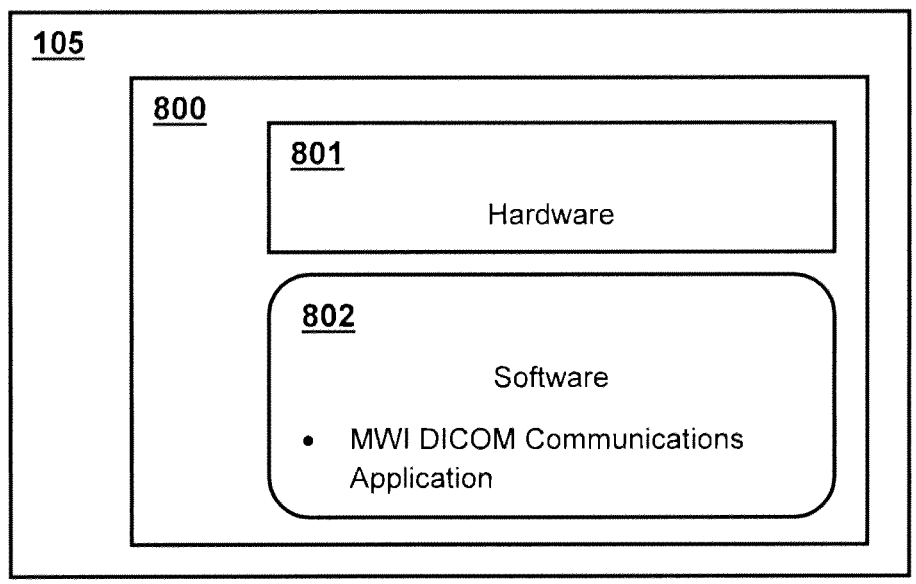
FIG. 8 is a block diagram of an exemplary computing device at the viewing location of a scientist/researcher.

FIG. 8 is a block diagram of an exemplary computing device 800 at the viewing location 105 of a scientist or researcher. The computing device 800 is preferably a networked computer with hardware 801 for connecting to a network, accepting input from a user, and displaying reconstructed images and other data to the scientist or researcher. The computing device 800 preferably includes software 802 that aids the scientist or researcher in viewing reconstructed images, and exchanging research data with the system. The MWI DICOM Communications Application is tailored for the scientist or researcher and allows for communications using the Digital Imaging and Communications in Medicine (DICOM) standard.

Figure 9:
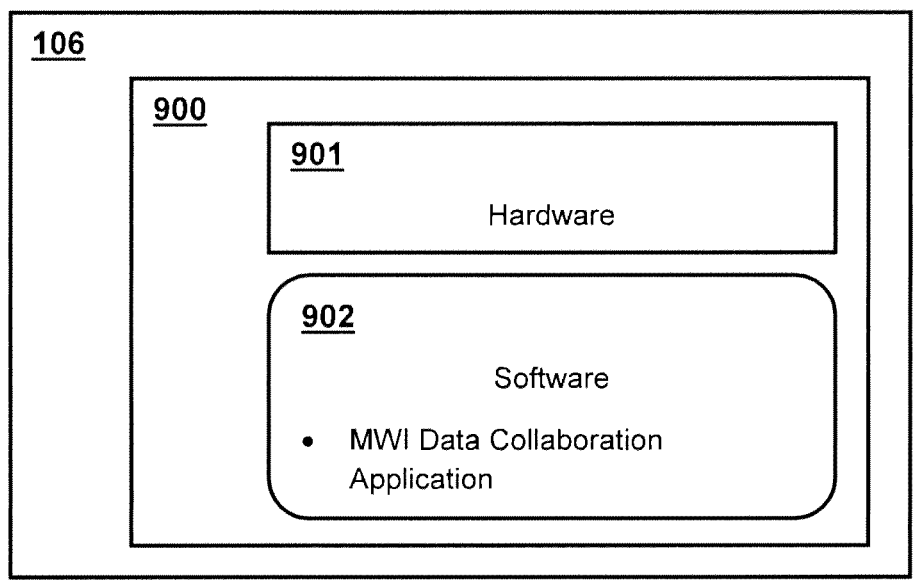
FIG. 9 is a block diagram of an exemplary computing device at the viewing location of an insurance company.

FIG. 9 is a block diagram of an exemplary computing device 900 at the viewing location 106 of an insurance company. The computing device 900 is preferably a networked computer with hardware 901 for connecting to a network, accepting input from a user, and displaying reconstructed images and other data to an insurance company agent. The computing device 900 preferably includes software 902 that aids the insurance company agent in exchanging insurance related data with the system. The MWI Data Collaboration Application is tailored for the insurance company agent and allows for communications using the insurance company standards.

The computing devices at the viewing locations 103-105 and at the insurance company 106 can be laptop or desktop computers, and the computers can be connected to the network via a wired or wireless connection.

Figure 10:
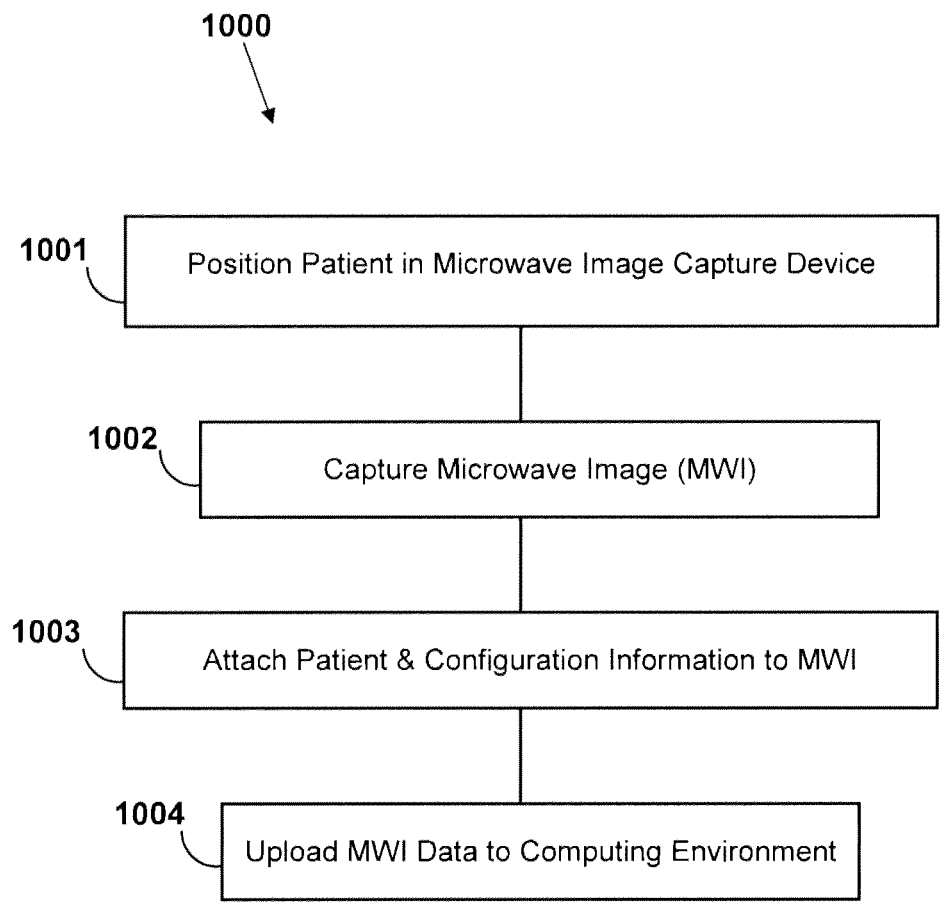
FIG. 10 is a flow chart of exemplary steps for use at the image acquisition site.

FIG. 10 is a flow chart 1000 of exemplary steps for use at an image data acquisition site 101. In step 1001, the patient is positioned in the microwave image capture device. In the case of a full body scanner, the patient lies down, on their back, on a moveable table that is part of the image capture device. In step 1002, microwave image data is captured by scanning all or part of the patient's body with the image capture device. The image capture device impinges electromagnetic radiation upon the patient, and the scattered electromagnetic radiation is collected by a series of antennas (or receivers) arranged within the image capture device. In step 1003, information identifying the patient is attached to the raw microwave image (MWI) data. Information regarding the configuration of the microwave image data capture device is also attached to the MWI data. In step 1004, the MWI data is uploaded to the Computing Environment for processing.

Figure 11A:
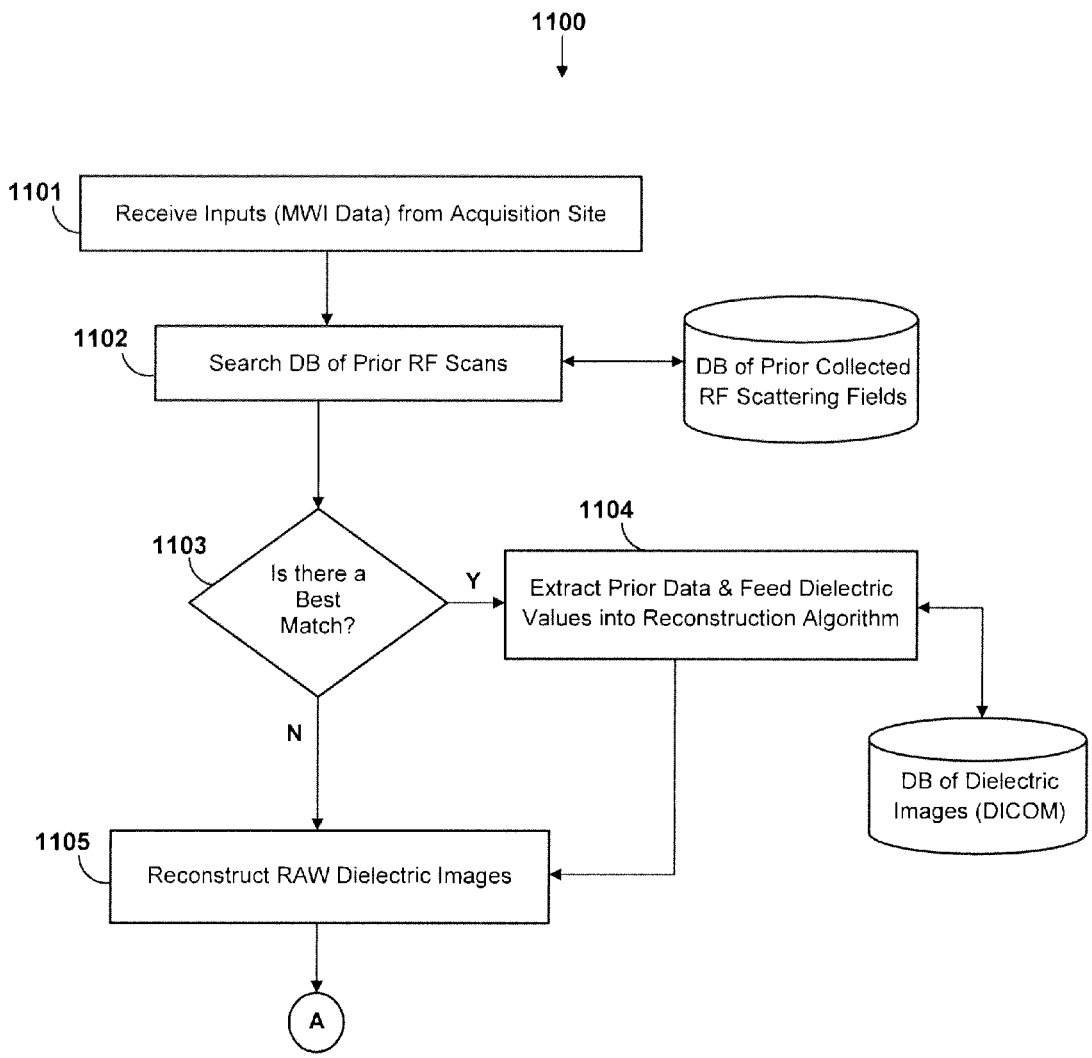
FIGS. 11A and B are flow charts of exemplary steps used at the computing environment.

FIG. 11A is a flow chart 1100 of exemplary steps used at the computing environment 102. It should be noted that since parallel processing is employed, the steps shown in the various flowcharts herein may not be performed in the sequence shown. In step 1101, MWI data from the image acquisition site are input to the computing environment.

The Input to reconstruction and learning algorithms includes:
1. RF scattering information measured from an antenna apparatus where the scattering object is either in a coupled or non-coupled media.
2. Three dimensional surface map of the scattering object obtained using optical or non-optical methods.
3. Positional information of RF emitters related to the collected scattering information.
4. Geometric parameters of the collection device (this is done in order to accommodate collection devices that are of different sizes and configurations).
5. RF and electrical characteristics of the RF emitters.
6. RF and electrical characteristics of the RF receivers.
7. Collection device calibration data.
8. Collection site specific data (location, phone numbers, POCs, etc.)
9. Scattering Object specific information:
    a. Object classification
        i. Human
        ii. Animal
        iii. Phantom
        iv. Other
    b. For patients (human or animal):
        i. Demographic information, sex, weight and appropriate patient identifiers used for identity management.
        ii. Any presenting symptoms, reasons for examination and any other pertinent previous health information.
        iii. Insurance/payment information.
    c. Phantom ID for calibration phantoms.
    d. Other data for other objects.
10. Requested study output—study type, orthogonal views, anatomy of interest, area of interest.

Input data is encoded according to the DICOM standard. Provisions are also made to handle other types of data encoding for data exchange such as HL7, XML, etc.

In step 1102, a database of prior RF scans is searched. This search involves looking for prior RF scans that are not just similar in electrical characteristics but also are similar in other characteristics including, patient sex, age, weight and location of the scanned data. The database of prior RF scans is essentially a database of the input data from step 1101. The input data also contains the prior RF scanned data including raw measured data. However, associating all the input data with the RF scans and saving in a database, allows searching and relating data upon other characteristics as mentioned above.

In step 1103, it is determined if there is a possible match that can be used. There is a computational component in this block that does further feature extraction and comparisons in order to ensure like data is being appropriately compared.

In step 1104, if a close match is found, the prior reconstructed data is retrieved from the database of dielectric images. Once this data is retrieved it is made available as a 'seed' into the reconstruction process, described further below.

As discussed above, this is a substantial feature because the iterative reconstruction processing takes substantially less time if a better seed (or starting point) is used. The database of dielectric images is a database of successfully reconstructed dielectric images. Associated with this data is the input data from step 1101.

In step 1105, the RAW dielectric images are reconstructed using MWI Reconstruction and Learning Algorithms. Detailed steps of image reconstruction are discussed in greater detail below in conjunction with FIGS. 12A and 12B.

Figure 11B:
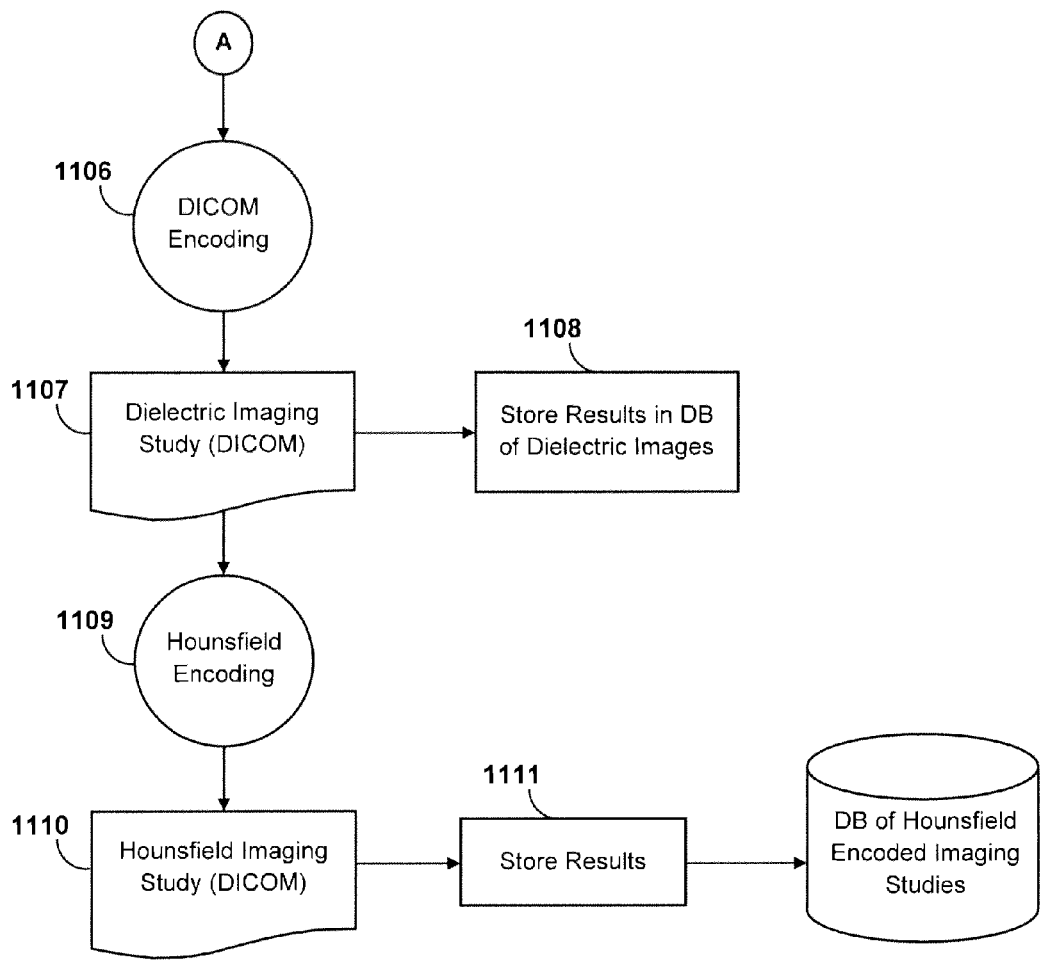

FIG. 11B is a continuation of flow chart 1100 that started in FIG. 11A. In step 1106, once the RAW dielectric imaging study has been reconstructed, it is encoded into the DICOM format and formatted according to the requested study output of step 1101. This process also standardizes the data and makes it more easily sharable with other DICOM applications. In step 1107, a final completed dielectric imaging study is now available in DICOM format. In step 1108, the DICOM dielectric imaging study is stored into the database of dielectric images.

In step 1109, Hounsfield encoding is performed. Hounsfield encoding is a step taken to relate the dielectric values of the image(s) reconstructed to an appropriate Hounsfield value. Hounsfield values are typically used in CT studies and are a unit of measure that represents the different density levels of tissues and/or other substances. In step 1110, using the Hounsfield encoded data; a DICOM formatted imaging study is created. The rational for Hounsfield encoding and putting into a DICOM format is to allow for the exchange of information created using MW techniques with current diagnostic tools and techniques. Additionally, the medical community is familiar with diagnosing Hounsfield imaging studies and hence physicians will require little if any retraining to use the output of the present MWI process. In step 1111, the DICOM Hounsfield imaging study is stored into a database of Hounsfield encoded imaging studies, which is a database of successfully reconstructed dielectric imaging studies encoded to Hounsfield units. Associated with the stored data is the input data from step 1101, less the RAW RF Scan data.

Figure 12A:
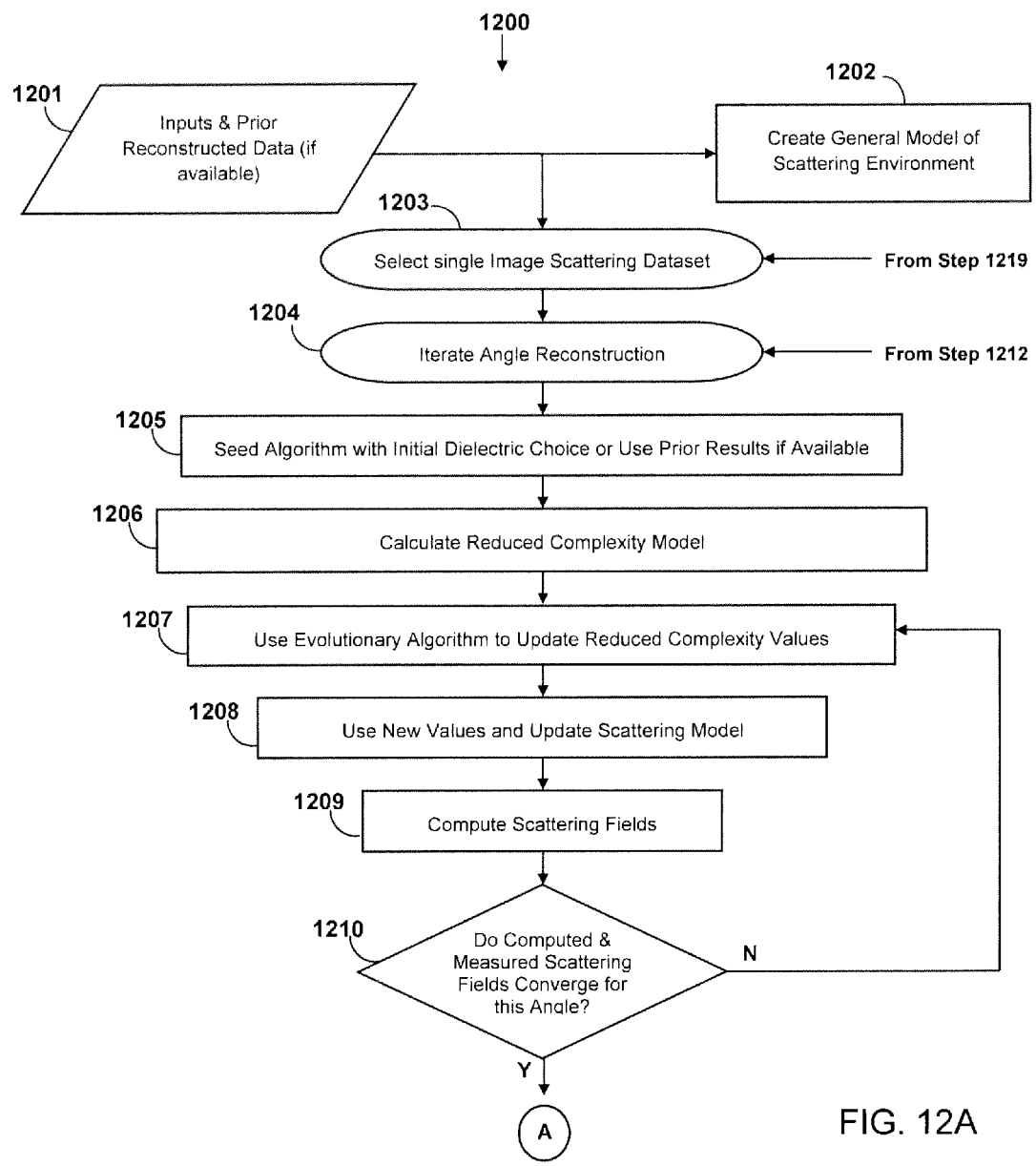
FIGS. 12A and B are flow charts showing steps used at the computing environment.

FIG. 12A is a flow chart 1200 showing steps used at the computing environment 102. This figure illustrates the combined use of the present MWI Reconstruction and Learning Algorithms in reconstructing RAW dielectric images, mentioned in step 1105 of FIG. 11A. In step 1201, the inputs from step 1101, as well as any prior reconstructed dielectric images from previous examinations, are received by the system for the Reconstruction of a RAW Dielectric Image. In step 1202, using the input values, this step sets up a forward scattering MW model based upon the characteristics of the scanning device. Additionally, calibration data and RF antenna characteristics are used in the model. In step 1203, this step starts the reconstruction for every image in the RF dataset. It does this by extracting information related to a single image scan from the RF dataset. The reconstruction algorithm will iterate through the RF dataset until all images have been reconstructed. In step 1204, each RF dataset for a single image is actually a set of collected data. For example, in one embodiment, there are many transmitter locations, many object "rotations," and many receivers. Data must be taken at many relative positions of the transmitters, object (patient) and receivers. This can be accomplished by moving the object and/or the transmitters and/or the receivers and/or by selective activation of transmitters and/or receivers. This collected dataset for a single image includes scattering data from these multiple observations. Each image dataset will have N translation scans. This is collected for M object "rotations." Hence there will be a total of N×M RF scattering samples for each image slice. In step 1205, if prior results are available they are used to seed the algorithm with representative dielectric values. If not, a seed dielectric value is created based upon object geometry and relative position in the 3-dimensional object. In step 1206, the overall image complexity is reduced. However, enough complexity is still maintained to accurately model scattering behavior in certain instances. It should be noted that object geometry is used in the construction of this data set as well. The main benefit of the Reduced Complexity model is that Evolutionary Algorithms perform better with a smaller number of variables to optimize. In step 1207, the Evolutionary Algorithm finds the optimal set of variables necessary to minimize the difference between the measured and calculated scattering fields. Steps 1208, 1209 and 1210 are actually part of the Evolutionary Algorithm approach and are presented here for completeness. In step 1208, the output of step 1207 is used to update the Scattering Model. New dielectric values are fed into the model created in step 1202. In step 1209, using the updated dielectric values, a new set of scattering values are calculated using the model of step 1202. In step 1210, Computed and Measured scattering fields are compared using a defined cost function. A value is determined and a decision is made about the similarities of each dataset. If it is decided that the fields do not converge, then flow returns to step 1207. If, however, it is decided that the fields do converge, then flow proceeds to step 1111, illustrated in FIG. 12B.

Figure 12B:
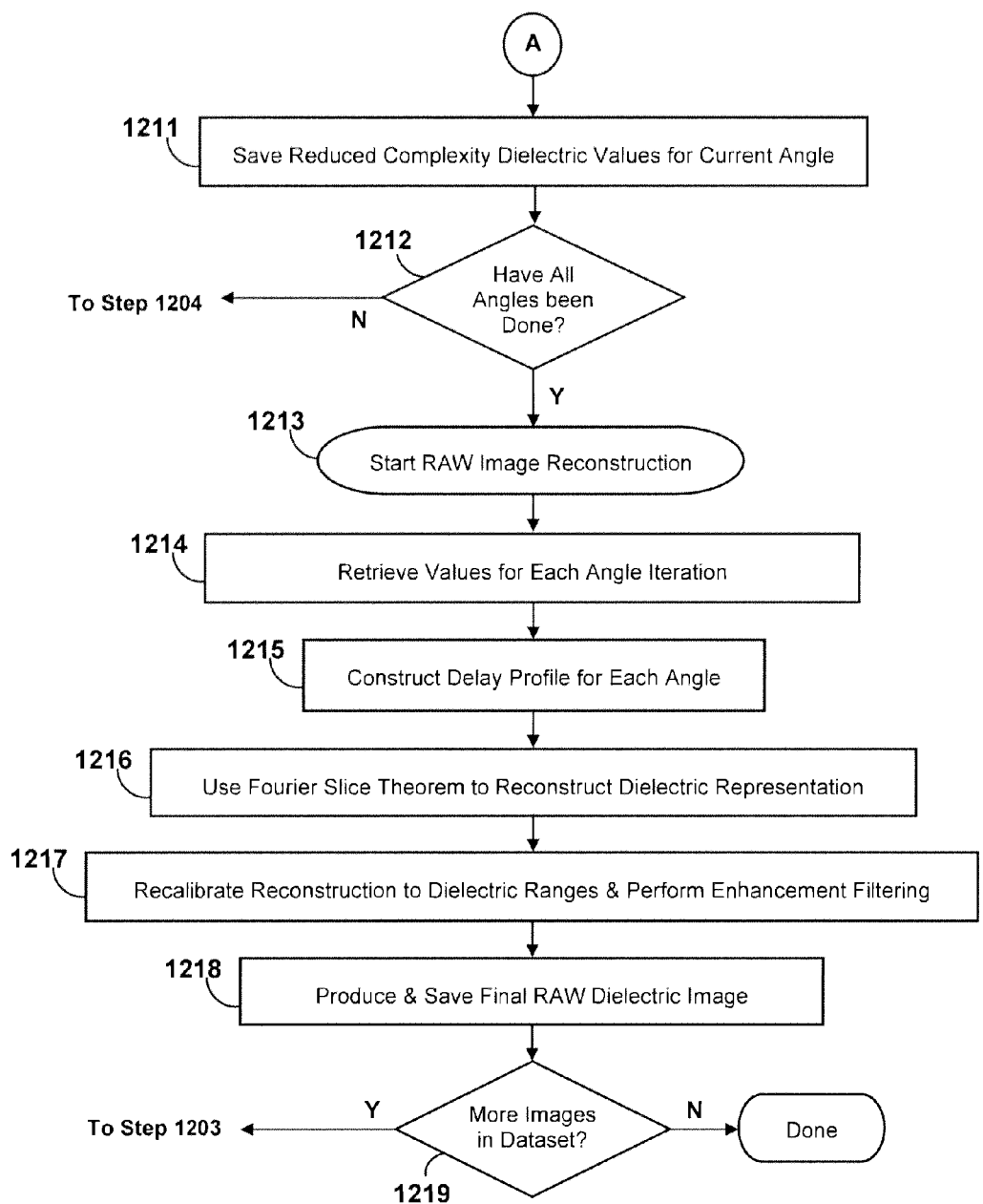

FIG. 12B is a continuation of flow chart 1200 that slatted in FIG. 12A. In step 1211, since datasets are found to be 'equal', the Reduced Complexity values for this angle rotation are saved. In step 1212, a check is done to ensure that all angles have been processed. If there are still more angles to be processed, then flow returns to step 1204. If, however, there are no more angles to process, then flow proceeds to step 1213. In step 1213, RAW image reconstruction is started. In step 1214, this step retrieves all the angle dependent reduced complexity dielectric values saved in step 1211. In step 1215, using the retrieved dielectric values from step 1214, a delay profile for each angle is calculated for each angle rotation. There is a delay profile for each angle rotation. This data is saved and used in the next step. In step 1216, using the Fourier slice Theorem, filtered back-projection, and the data produced in step 1215, an image representative of the object's dielectric values is constructed. In step 1217, this step recalibrates the image created in step 1216 into true dielectric values. Also, any image processing required to improve the image for presentation is performed here. In step 1218, this is the output from 1217 plus this incorporates other necessary meta-information into the image structure so that the RAW image (without Hounsfield encoding or DICOM encoding) can be used later. The RAW image is also stored for later processing. In step 1219, a check is performed to see if more angles need to be processed. If more angles need processing, flow returns to step 1203. If, however, all angles have been processed, then reconstruction is done.

Figure 13:
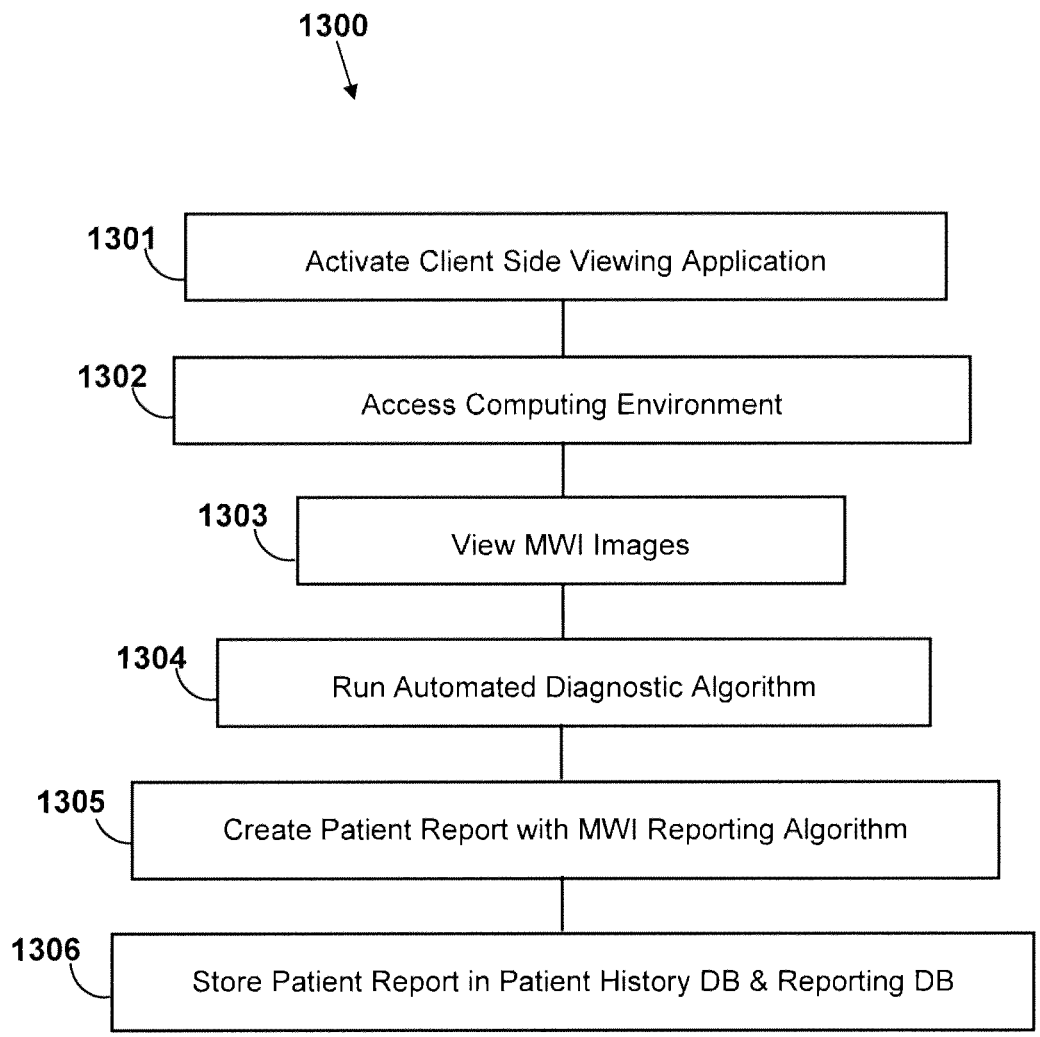
FIG. 13 is a flow chart of exemplary steps for use at the viewing location of a medical professional.

FIG. 13 is a flow chart 1300 of exemplary steps for use at the viewing location of a medical professional. In step 1301, the medical professional activates his Viewing Application in order to bring up a graphical user interface that he or she can use to interact with the present system. In step 1302, the medical professional signs-in to the system and a connection is made to the Computing Environment 102. In step 1303, the medical professional selects a patient and a relevant image of the patient for viewing. In step 1304, the medical professional is given the option to run an Automated Diagnostic Algorithm to help the professional form a diagnosis of the patient. As discussed above, if the centralized database includes prior images and prior diagnosis and other information from a plurality of sites 101, the automated diagnostic algorithm is able to make a more informed suggested diagnosis. The Diagnostic Algorithm can access the patient's history to track changes in images of the patient. The Diagnostic Algorithm can also use information from other sources to identify features and anomalies in the patient's image. In step 1305, the medical professional can write a report on the patient using the MWI Reporting Algorithm. The Reporting Algorithm provides the professional with multiple pre-formatted reports that can be customized for the professional. In step 1306, once the report has been completed, the medical professional is requested to store the report in the Patient History Database and in the Reporting Database. The final report also becomes part of the Patient Diagnostic Learning Algorithm to support automated diagnostic capabilities.

Figure 14:
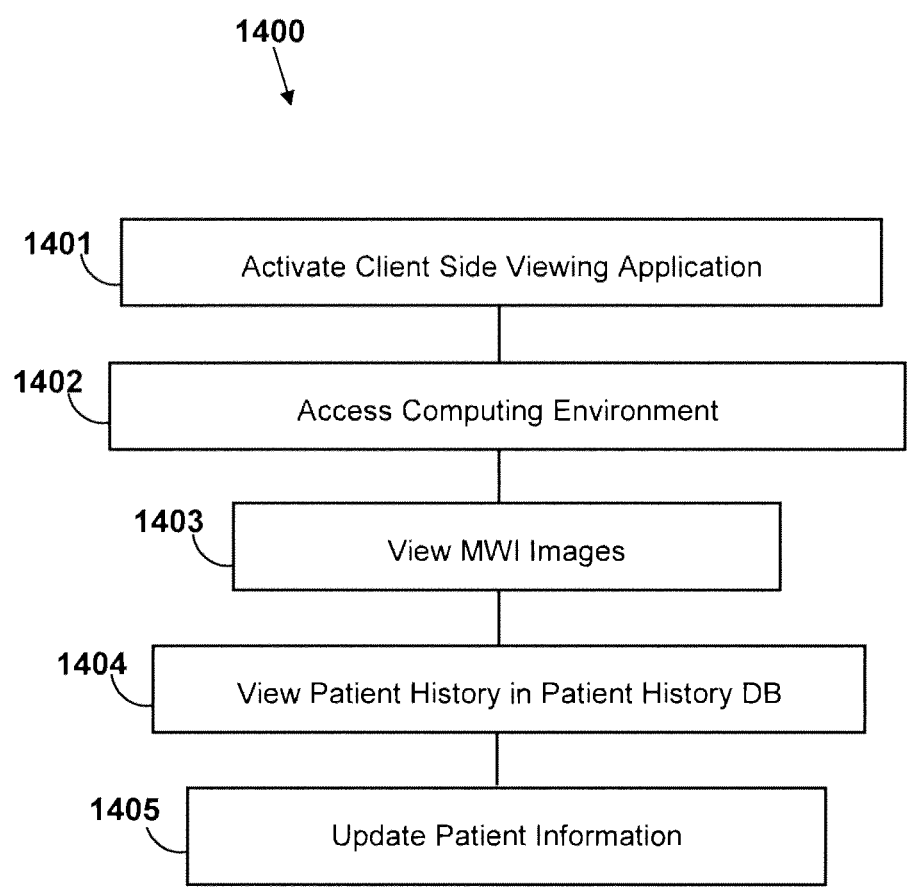
FIG. 14 is a flow chart of exemplary steps for use at the viewing location of a patient.

FIG. 14 is a flow chart 1400 of exemplary steps for use at the viewing location of a patient. In step 1401, the patient activates her Viewing Application in order to bring up a graphical user interface that she can use to interact with the present system. In step 1402, the patient signs-in to the system and a connection is made to the Computing Environment 102. In step 1403, the patient interacts with the Viewing Application in order to select an image for viewing. In step 1404, the patient is able to access the Patient History Database in order to review the patient's reports that have been submitted by medical professionals. In step 1405, the patient is allowed to update their own personal information with any changes or new patient information.

Figure 15:
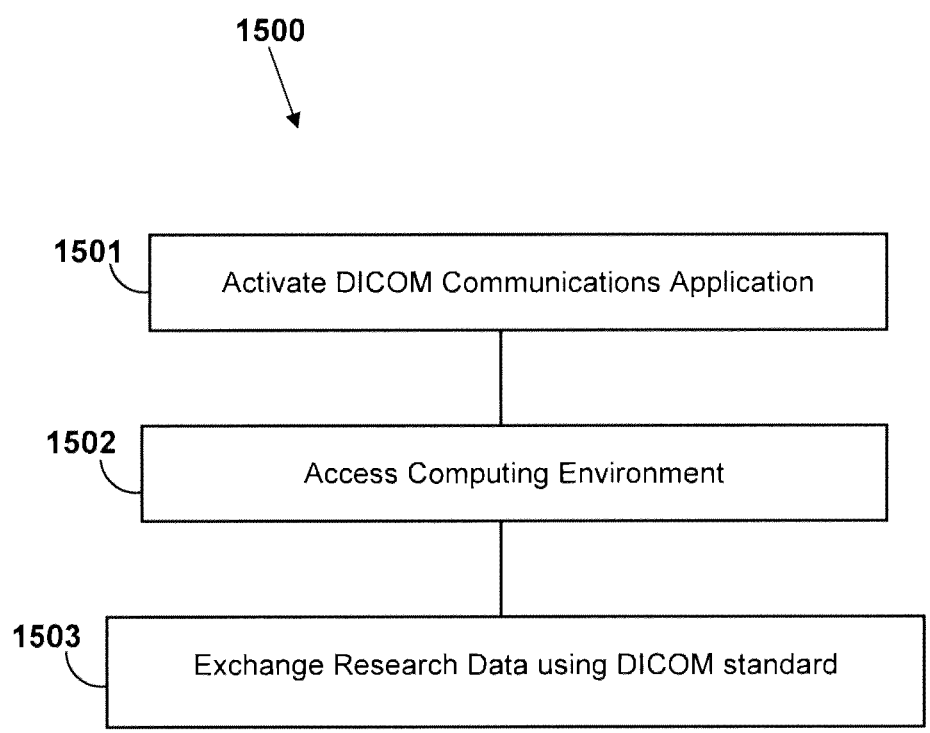
FIG. 15 is a flow chart of exemplary steps for use at the viewing location of a scientist or researcher; and, FIG. 16 is a flow chart of exemplary steps for use at the viewing location of an insurance company.

FIG. 15 is a flow chart 1500 of exemplary steps for use at the viewing location of a scientist or researcher. In step 1501, the researcher activates their Viewing Application in order to bring up a graphical user interface that they can use to interact with the present system. In step 1502, the researcher signs-in to the system and a connection is made to the Computing Environment 102. In step 1503, the researcher exchanges scientific data with the present system. The MWI DICOM Communications application supports the DICOM industry standard data exchange with Researchers, Hospitals and Clinics.

Figure 16:
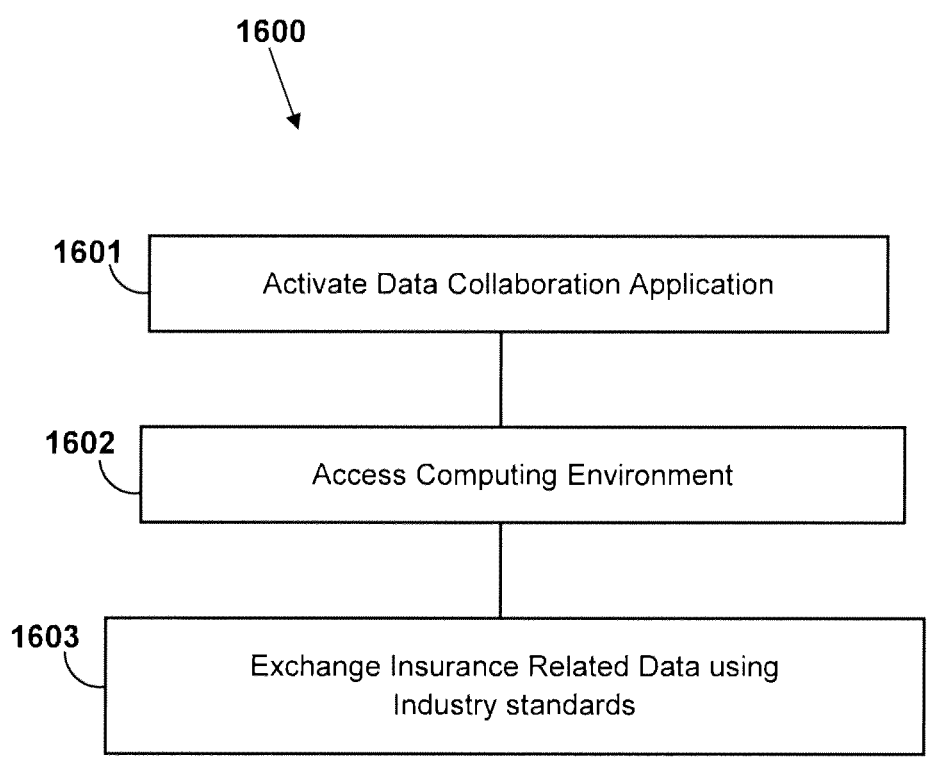

FIG. 16 is a flow chart 1600 of exemplary steps for use at the viewing location of an insurance company. In step 1601, the insurance agent activates their Data Collaboration Application in order to bring up a graphical user interface that they can use to interact with the present system. In step 1602, the agent signs-in to the system and a connection is made to the Computing Environment 102. In step 1603, the insurance agent exchanges data with the present system using insurance industry standards. The MWI Data Collaboration application is designed to support and provide responses to inquiries from Insurers.

The present distributed microwave image processing has numerous advantages over traditional systems that effectively put it in a new class of image processing. The computational difficulties associated with microwave imaging had previously made it impossible to use this technology effectively for clinical purposes. However CBMWIP enables the use of MWIP for clinical purposes. The particular composition and configuration of CBMWIP accounts for the necessary business processes that are required to make use of MWI data and provide that capability in an economically feasible package. The advantages provided by the present system to the imaging community include:

CBMWIP uses cloud technology to distribute the computationally intensive Image Reconstruction Algorithm and Learning Algorithm;

The Image Reconstruction Algorithm provides reconstruction of raw data into higher resolution images than previously possible;

The Learning Algorithm speeds the image reconstruction;

Allows for the decoupling of the microwave scanning device from the MWI reconstruction process;

Allows for the decoupling of image viewing of reconstructed MWIs from user's computer resources;

Allows for installation of scanning devices in less environmentally stringent conditions since specialized computer resources are removed from the scanner location;

Provides a centralized database of patient image history from scanning devices that are used to aid the diagnostic process;

Allows for clinicians to access a patient's reconstructed microwave images and history for diagnostic purposes;

Allows for clinicians to store diagnostic reports;

Allows for patients to access their reconstructed microwave images and history for medical purposes;

Allows for other imaging systems in clinical locations to access the reconstructed MWI for diagnostic or reference purposes using the DICOM standard; and, Allows for learning algorithms to use stored diagnostic reports to aid automated diagnostic capabilities.

The invention is not limited to the embodiments described above. Instead, many other variations of the invention are within the scope and spirit of the invention. The invention is therefore defined with reference to the following claims.

What is claimed is:

1. A system for producing images of at least part of a body of a patient, the system comprising:
   a plurality of remote data acquisition sites, each of the plurality of remote data acquisition sites comprising
      at least one microwave transmitter and at least one microwave receiver configured to transmit a microwave to a body and to receive a microwave from the body and to generate microwave data, and
      wherein the plurality of remote data acquisition sites are configured to transmit the microwave data; and
   at least two centralized processors, configured to receive the transmitted microwave data from the plurality of remote data acquisition sites, wherein the at least two centralized processors are specially configured to receive the microwave data and iteratively reconstruct images based on at least both of (1) the microwave data and (2) stored data of a prior microwave image reconstruction of a different patient which closely matches data of the patient to seed a current iterative reconstruction.

2. A system as set forth in claim 1, wherein the at least two centralized processors comprises:
a network interface configured to transmit a reconstructed microwave image to a remote viewing location.

3. A system as set forth in claim 1, wherein the at least two centralized processors comprises:
at least two high-speed memory buses, and a plurality of memories that are connected to the processors by the high-speed memory buses.

4. A system as set forth in claim 1, further comprising processing hardware forming at least one processing queue that receives microwave data from the plurality of remote data acquisition sites and provides the microwave data to the at least two centralized processors such that the processors operate in parallel on the microwave data.

5. A system as set forth in claim 1, wherein the at least two centralized processors are configured to accept and respond to insurance inquiries.

6. A system as set forth in claim 1, wherein the at least two centralized processors are configured to convert data into a DICOM (digital imaging and communications in medicine) form that allows researchers and scientists to access the system.

7. A system as set forth in claim 1, wherein the at least two centralized processors comprises:
multi-core processors.

8. A system as set forth in claim 1, wherein the at least two centralized processors are configured to receive, from the remote data acquisition sites, information specifying configurations of the at least one microwave transmitter and the at least one microwave receiver at the remote data acquisition sites.

9. A system for producing images of at least part of a body, the system comprising:
a plurality of remote data acquisition sites, each of the plurality of remote data acquisition sites comprising
at least one microwave transmitter and at least one microwave receiver configured to transmit a microwave to a body and to receive a microwave from the body and to generate microwave data, and
wherein the plurality of remote data acquisition sites are configured to transmit the microwave data; and
at least two centralized processors, configured to receive the transmitted microwave data from the plurality of remote data acquisition sites, wherein the at least two centralized processors are specially configured to receive the microwave data and reconstruct at least one image based on the microwave data,
wherein the at least two centralized processors comprises:
a centralized database configured to store microwave data and reconstructed dielectric images of prior microwave scans performed at the plurality of remote data acquisition sites, the microwave data including at least scattering fields of the prior microwave scans; and
wherein the centralized processors are configured to determine a seed for iterative microwave reconstruction of an image for a current microwave scan, the seed determination including at least both of (1) comparing scattering fields of the current microwave scan to scattering fields of prior microwave scans stored in the centralized database to find a best match and (2) using a prior reconstructed dielectric image that was previously reconstructed from the scattering fields of the best match.

10. A system for producing images of at least part of a body, the system comprising:
a plurality of remote data acquisition sites, each of the plurality of remote data acquisition sites comprising
at least one microwave transmitter and at least one microwave receiver configured to transmit a microwave to a body and to receive a microwave from the body and to generate microwave data, and
wherein the plurality of remote data acquisition sites are configured to transmit the microwave data; and
at least two centralized processors, configured to receive the transmitted microwave data from the plurality of remote data acquisition sites, wherein the at least two centralized processors are specially configured to receive the microwave data and reconstruct at least one image based on the microwave data,
wherein the at least two centralized processors comprises:
a searchable database containing stored data including scattering fields of prior microwave scans, prior reconstructed dielectric images, and patient characteristics, the stored data configured to be searchable by scattering fields of prior microwave scans and patient characteristics,
wherein the centralized processors are configured to search the searchable database and use search results to retrieve a prior reconstructed dielectric image to use as a seed for iterative image reconstruction to reconstruct at least one image based on the microwave data.

11. A system for producing images of at least part of a body, the system comprising:
a plurality of remote data acquisition sites, each of the plurality of remote data acquisition sites comprising
at least one microwave transmitter and at least one microwave receiver configured to transmit a microwave to a body and to receive a microwave from the body and to generate microwave data, and
wherein the plurality of remote data acquisition sites are configured to transmit the microwave data; and
at least two centralized processors, configured to receive the transmitted microwave data from the plurality of remote data acquisition sites, wherein the at least two centralized processors are specially configured to receive the microwave data and reconstruct at least one image based on the microwave data,
wherein the at least two centralized processors are specially configured to reconstruct from the microwave data at least one image represented in dielectric values, and to convert the image represented in dielectric values to an image represented in Hounsfield units.

12. A method for producing images of at least part of a body of a patient, the method comprising:
collecting microwave data at a plurality of remote data acquisition sites by transmitting microwaves using at least one microwave transmitter and receiving microwaves using at least one microwave receiver;
transmitting the collected microwave data from the plurality of remote data acquisition sites; and
receiving the transmitted microwave data from the plurality of remote data acquisition sites in at least two centralized processors specially configured to receive the microwave data and iteratively reconstructing images based on at least both of (1) the microwave data and (2) stored data of a prior microwave image reconstruction of a different patient which closely matches data of the patient to seed a current iterative reconstruction.

13. A method as set forth in claim 12, wherein the method comprises:
generating microwave images in a DICOM (digital imaging and communications in medicine) compatible format.

14. A method as set forth in claim 12, wherein the method further comprises receiving in the at least two centralized processors, from the remote data acquisition sites, information specifying configurations of the at least one microwave transmitter and the at least one microwave receiver at the remote data acquisition sites.

15. A method for producing images of at least part of a body, the method comprising:
collecting microwave data at a plurality of remote data acquisition sites by transmitting microwaves using at least one microwave transmitter and receiving microwaves using at least one microwave receiver;
transmitting the collected microwave data from the plurality of remote data acquisition sites; and
receiving the transmitted microwave data from the plurality of remote data acquisition sites in at least two centralized processors specially configured to receive the microwave data and reconstruct at least one image based on the microwave data to generate a reconstructed image,
wherein the method comprises:
storing microwave data and reconstructed dielectric images of prior microwave scans performed at the plurality of remote data acquisition sites in a centralized database;
comparing at least scattering fields of a current microwave scan to scattering fields of prior microwave scans stored in the centralized database; and
determining a seed for iterative microwave reconstruction of an image for the current microwave scan based on a prior reconstructed dielectric image that was previously reconstructed from prior scattering fields identified in said comparison.

16. A method for producing images of at least part of a body, the method comprising:
collecting microwave data at a plurality of remote data acquisition sites by transmitting microwaves using at least one microwave transmitter and receiving microwaves using at least one microwave receiver;
transmitting the collected microwave data from the plurality of remote data acquisition sites; and
receiving the transmitted microwave data from the plurality of remote data acquisition sites in at least two centralized processors specially configured to receive the microwave data and reconstruct at least one image based on the microwave data to generate a reconstructed image represented in dielectric values,
wherein the method comprises:
converting the reconstructed image represented in dielectric values to an image represented in Hounsfield units.

17. A system for producing images of at least part of a body, the system comprising:
a plurality of remote data acquisition sites, each of the plurality of remote data acquisition sites comprising
at least one microwave transmitter and at least one microwave receiver configured to transmit a microwave to a body and to receive a microwave from the body and to generate microwave data, and
wherein the plurality of remote data acquisition sites are configured to transmit the microwave data;
at least two centralized processors, configured to receive the transmitted microwave data from the plurality of remote data acquisition sites, wherein the at least two centralized processors are specially configured to receive the microwave data and reconstruct at least one image based on the microwave data; and
a centralized database configured to store microwave data and reconstructed dielectric images of prior microwave scans performed at the plurality of remote data acquisition sites, the microwave data including at least scattering fields of the prior microwave scans;
wherein the at least two centralized processors are configured to compare scattering fields of a current microwave scan to scattering fields of prior microwave scans stored in the centralized database to determine a closest match, wherein a prior reconstructed dielectric image that was previously reconstructed from the scattering fields of the closest match is utilized to generate a seed for reconstructing a microwave image of the current microwave scan.

* * * * *